US008068015B2

(12) United States Patent
Burg (10) Patent No.: US 8,068,015 B2
(45) Date of Patent: Nov. 29, 2011

(54) MEDICATION DISPENSER RESPECTING THE PHYSIOLOGICAL CLOCK OF PATIENTS

(75) Inventor: Bernard Burg, Menlo Park, CA (US)

(73) Assignee: Panasonic Corporation, Osaka (JP)

( * ) Notice: Subject to any disclaimer, the term of this patent is extended or adjusted under 35 U.S.C. 154(b) by 851 days.

(21) Appl. No.: 11/843,306

(22) Filed: Aug. 22, 2007

(65) Prior Publication Data

US 2009/0050645 A1 Feb. 26, 2009

(51) Int. Cl.
*G08B 1/00* (2006.01)
(52) U.S. Cl. ............... 340/309.16; 340/539.12; 368/10; 221/2; 700/231
(58) Field of Classification Search .............. 340/309, 340/539.12; 221/2, 3, 15; 368/10; 700/231, 700/239, 240, 242, 244; 706/21, 924; 358/10
See application file for complete search history.

(56) References Cited

U.S. PATENT DOCUMENTS

| | | | | |
|---|---|---|---|---|
| 5,646,912 A * | 7/1997 | Cousin | ............................ | 368/10 |
| 5,990,782 A * | 11/1999 | Lee | ............................ | 340/309.7 |
| 6,604,650 B2 * | 8/2003 | Sagar | ............................ | 221/3 |
| 6,771,174 B2 * | 8/2004 | Broas | ............................ | 340/573.1 |
| 7,301,463 B1 * | 11/2007 | Paterno | ............................ | 340/573.1 |
| 7,330,101 B2 * | 2/2008 | Sekura | ............................ | 340/309.4 |
| 7,440,817 B2 * | 10/2008 | Fu | ............................ | 700/237 |
| 2002/0027507 A1 * | 3/2002 | Yarin et al. | ............................ | 340/573.1 |
| 2004/0015132 A1 * | 1/2004 | Brown | ............................ | 604/131 |
| 2005/0119604 A1 * | 6/2005 | Bonney et al. | ............................ | 604/19 |
| 2005/0187789 A1 * | 8/2005 | Hatlestad et al. | ............................ | 705/2 |
| 2005/0278409 A1 * | 12/2005 | Kutzik et al. | ............................ | 709/200 |
| 2005/0286686 A1 * | 12/2005 | Krstulich | ............................ | 379/32.01 |
| 2008/0091470 A1 * | 4/2008 | Muradia | ............................ | 705/3 |

* cited by examiner

*Primary Examiner* — Daniel Wu
*Assistant Examiner* — Nay Tun
(74) *Attorney, Agent, or Firm* — Harness, Dickey & Pierce, P.L.C.

(57) ABSTRACT

A medication dispensing system for use with a medication dispenser, includes a physiological module and an ingestion module. The physiological module receives information regarding time-based medication intake, information regarding event-based medication prescription, and sensory input indicating occurrences of events indicative of a patient's physiological condition and/or the patient's physiological clock. The physiological module then determines physiological event-based medication intake based on the information regarding the event-based medication prescription and physiological rules regarding the patient's physiological condition and/or the patient's physiological clock. The ingestion module merges event-based medication intake and time-based medication intake by delaying or accelerating dispensing of a time-based medication. The delay or acceleration can be applied to ensure that the time-based medication is dispensed at the same time as an event-based medication, and/or in order to increase a time difference between ingestion of the time-based medication and the event-based medication.

15 Claims, 8 Drawing Sheets

MEDICATION DISPENSER RESPECTING THE PHYSIOLOGICAL CLOCK OF PATIENTS

FIELD

The present disclosure generally relates to medication dispensers, and relates in particular to medication dispenser that can dynamically determine a user's physiological clock and dispense medication according to the physiological clock.

BACKGROUND

The statements in this section merely provide background information related to the present disclosure and may not constitute prior art.

Figure 8:
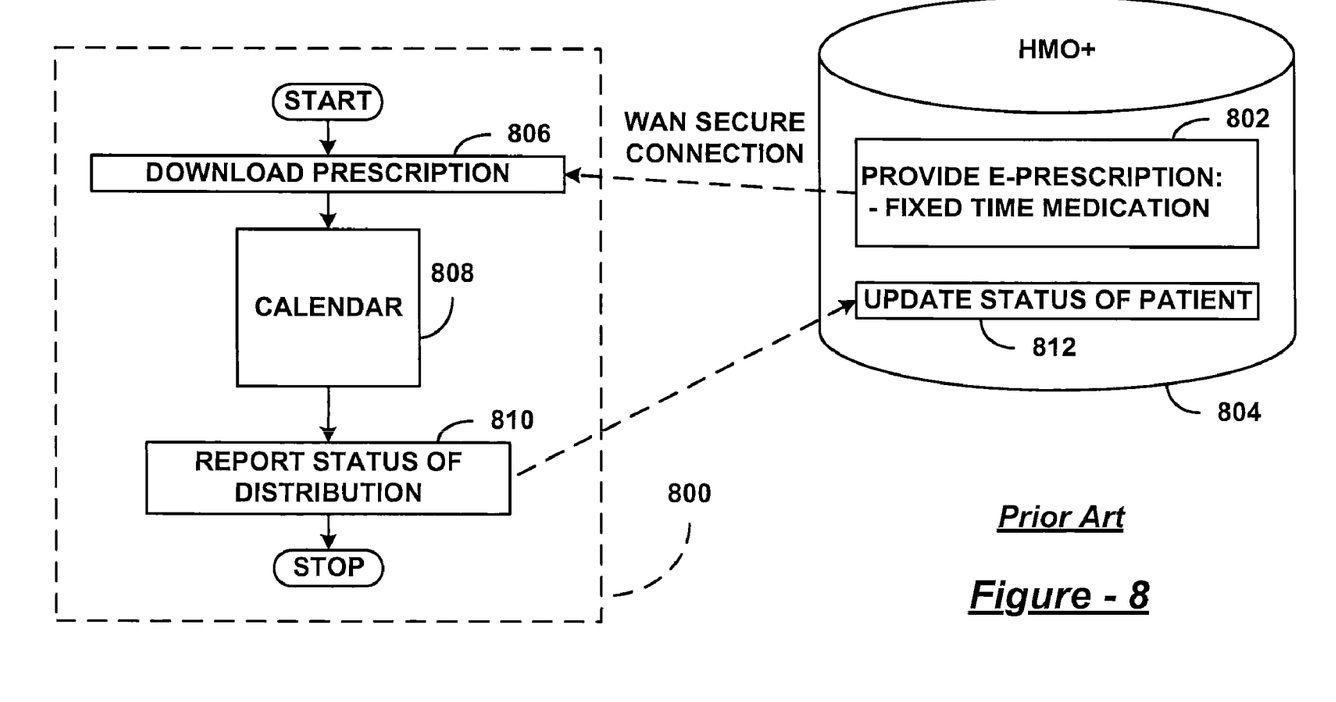
FIG. 8 is a block diagram illustrating a medication dispenser according to the prior art.

Referring to FIG. 8, existing medication dispensers dispense medication according to a calendar. Hence they force patients into a very strict daily routine, as the medication ingestion has been set for fixed times. This rigidity and the unnecessary constraints imposed on patients are amongst the causes of low observance of medication prescriptions.

Today's typical medication dispenser 800 can read an e-prescription 802 at an external site like a health monitoring organization or a hospital 804 (hereinafter referred to as HMO+). This prescription 802 can specify fixed times for administering medications, and can be downloaded at step 806 into a calendar 808 scheduling the medication ingestion at fixed hours. At step 810, the effective medication intake can be reported back to the HMO+ 804, which can then update the status of the patient at step 812.

SUMMARY

A medication dispensing system for use with a medication dispenser includes a physiological module and an ingestion module. The physiological module receives information regarding time-based medication intake, information regarding event-based medication prescription, and sensory input indicating occurrences of events indicative of a patient's physiological condition and/or the patient's physiological clock. The physiological module then determines physiological event-based medication intake based on the information regarding the event-based medication prescription and physiological rules regarding the patient's physiological condition and/or the patient's physiological clock. The ingestion module merges event-based medication intake and time-based medication intake by delaying or accelerating dispensing of a time-based medication. The delay or acceleration can be applied to ensure that the time-based medication is dispensed at the same time as an event-based medication, and/or in order to increase a time difference between ingestion of the time-based medication and the event-based medication.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Some medication should be administered according to the patient physiological cycle, e.g. before meals, during meals, after meals, in between meals, before sleep, not before driving etc., as well as in a sequence to increase the patient comfort or other parameters like the efficiency of the treatments, or to minimize discomfort. Existing medication dispensers are not capable of accommodating a patient's physiological cycle. Today's medication dispenser base medication intake solely on a calendar.

Figure 1:
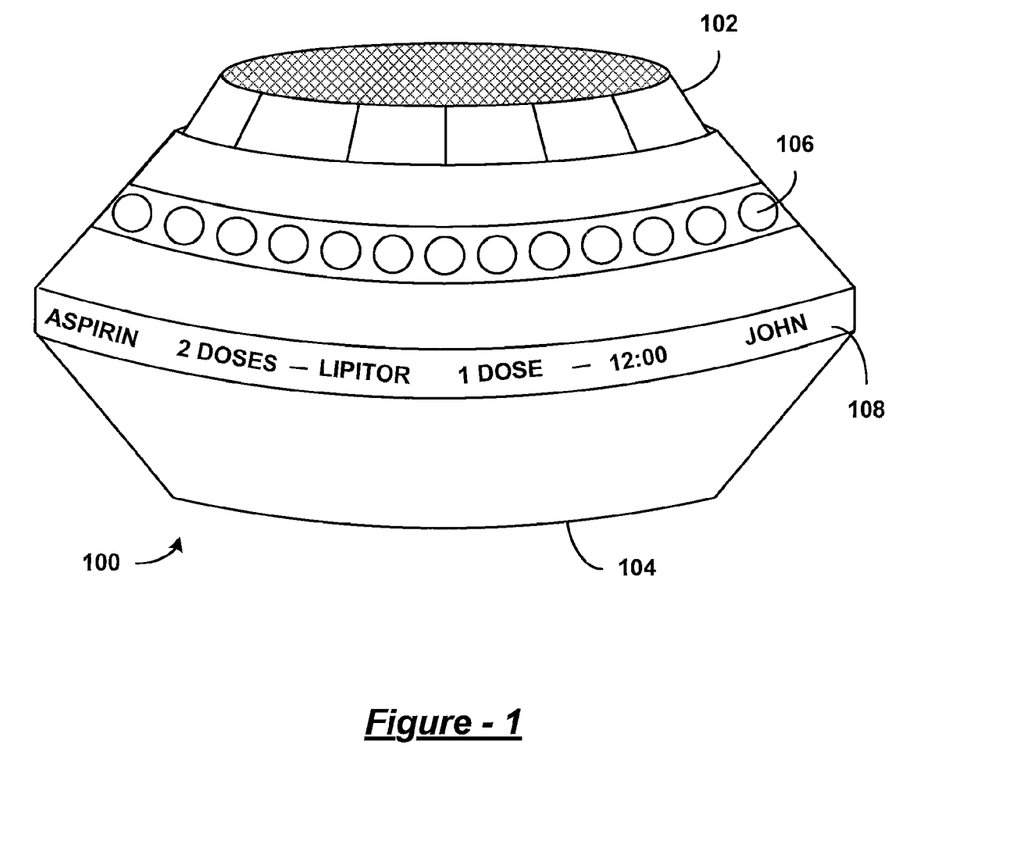
FIG. 1 is a view illustrating a medication dispenser.

Referring to FIG. 1, it is envisioned that some embodiments can relate to a wearable, ambient medication dispenser 100 that can be held, for example, in a user's hand. In some embodiments, a medication release button 102 can be actuated by the other of the user's hands to accomplish release of medication via medication exit 104. In some embodiments, the medication release button can glow and/or flash various colors to indicate status of the patient. In alternative or additional embodiments, a light source array 106 of LEDs or other light sources can be provided that can glow and/or flash various colors to indicate status of the patient. In alternative or additional embodiments, a display 108 can be provided for providing details Turning now to FIG. 2, it is envisioned that a medication dispenser can take various forms. In some embodiments, the medication dispenser can hold and dispense medication. In alternative or additional embodiments, a medication dispenser can inform a user when the user should take medication, and which medications to take. It is envisioned that the medication dispenser can take the form of a software system on a home network or Internet service that can communicate with a cellular telephone carried by the user. It is alternatively or additionally envisioned that the medication dispenser can communicate (e.g., a WAN secure connection) with an HMO+ 202 to: (a) download at step 204 an e-prescription 206 from the HMO+ 202; and (b) update status of the patient at step 208 by reporting medication distribution status at step 209.

Figure 2:
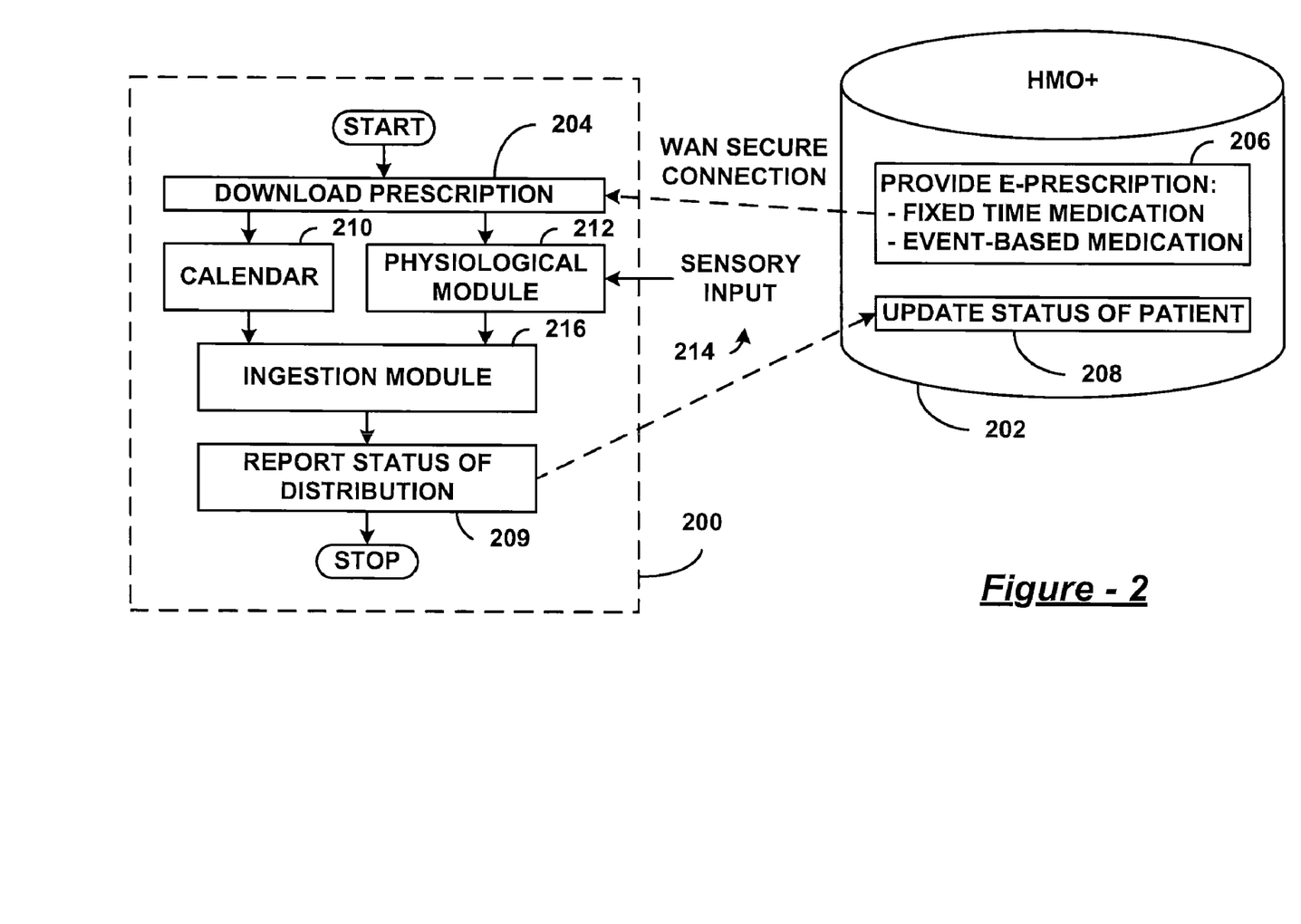
FIG. 2 is a block diagram illustrating a medication dispenser interacting with an HMO+.

In contrast to today's medication dispensers, the e-prescription 206, in addition to specifying a fixed time medication distribution schedule, can specify event-based medication distribution. Fixed time ingestion is well suited for medication controlling time-related parameters. An example language for the e-prescription content specifying a fixed time medication distribution schedule follows:

| Language for fixed time e-prescriptions: |
| --- |
| Take medication <X> at time <t><br>Take medication <X> at frequency <t> between [<time 1> and <time 2>]<br>Take medication <X> at <N> times a day <t> |

Classic Medication dispensers map these prescriptions to a calendar and therefore lock users into rigid schedules forcing users to freeze their breakfast, lunch and dinner times as well as sleeping habits to abide by the calendar.

Due to different physical, chemical and biological properties of medication, some medications need to be taken on a full stomach, some on an empty stomach or more generally according to the physiological clock of the body. For example, some medications need to be taken before, during, after meals or in between meals (e.g., vitamins between meals). Also, some medications need to be taken before or after sleeping (e.g., Vitamin C prevents sleeping). Further, some medications need to be taken when a physiological parameter triggers an alert (e.g., blood pressure is high/low).

In addition to existing time-based mechanisms, a new medication dispenser can dispense medication at the right moment by adapting it to the patient's life cycle as well as by handling exceptions (e.g., missed dose (brunch replacing breakfast and lunch) and medication incompatibilities overdoses and side effects). An example language for the e-prescription content specifying event-based medication distribution information follows:

| Language for event-based e-prescriptions: |
| --- |
| Take medication <X><br>   [before \| during \| after] [meal \| sleep \| physiological parameter \| medication <A>]<br>     forgot [jump \| take immediately \| take medication <B> \| call #1]<br>     overdose [symptom \| physiological parameter] actions [take medication <C> \| call #2]]<br>     side effect [symptom \| physiological parameter] actions [take medication <D> \| call #3]] |

Download of the e-prescription at step 204 can thus provide the fixed time distribution schedule to a calendar 210, and can provide the event-based distribution information to a physiological module 212. The physiological module 212 can receive sensory input 214 indicating events, such as by: responding to a patient's physiological condition (e.g., blood pressure level, heart attack); and/or dynamically determining a patient's physiological clock. Physiological module 212 can determine physiological event-based medication intake based on physiological rules regarding the patient's physiological condition and/or the patient's physiological clock.

An ingestion module 216 can merge physiological intake and fixed time medication intake to optimize parameters like comfort of users and/or efficiency of medication, allergies, etc. For example, the ingestion module 216 can receive from the calendar 210 one or more lists of medication to be dispensed at given times. Also, the ingestion module 216 can receive from physiological module 212 lists of medication to be dispensed immediately and/or at given times. In contrast to the given times indicated by the calendar 210, the given times indicated by the physiological module 214 can be dynamically determined based on sensed input indicating the patient's biological clock. Then, ingestion module 210 can, for example, decide to delay or accelerate dispensing fixed time medications so that the fixed medications are dispensed at the same time as the event based medication. In this case, a predetermined temporal window, such as one hour before and after a scheduled meal, can be employed to determine when to delay or accelerate dispensing the fixed time medications.

Alternatively or additionally, ingestion module can recognize that two medications, one a fixed time medication and the other an event based medication, have a possibility of producing an allergic reaction or other side effect when consumed together. In this case, ingestion module can decide to delay or accelerate dispensing of the fixed time medication in order to increase a time difference between ingestion of the fixed time medication and the event based medication.

Alternatively or additionally, ingestion module 216 can regard dispensing of some medications with higher priority than others. For example, dispensing ulcer medication at mealtimes can be given a higher priority than fixed time medications. In this case, dispensing the fixed time medications can be accelerated or delayed to coincide with dispensing of the ulcer medication, as opposed to the delaying or accelerating dispensing of the ulcer medication to coincide with dispensing of the fixed time medication. Also, dispensing aspirin during a sensed heart attack can have a higher priority than, for example, dispensing ulcer medication. In this case, for example, dispensing the aspirin will not be delayed until time to dispense the ulcer medicine, even if the time to dispense the ulcer medicine is very soon.

Figure 3:
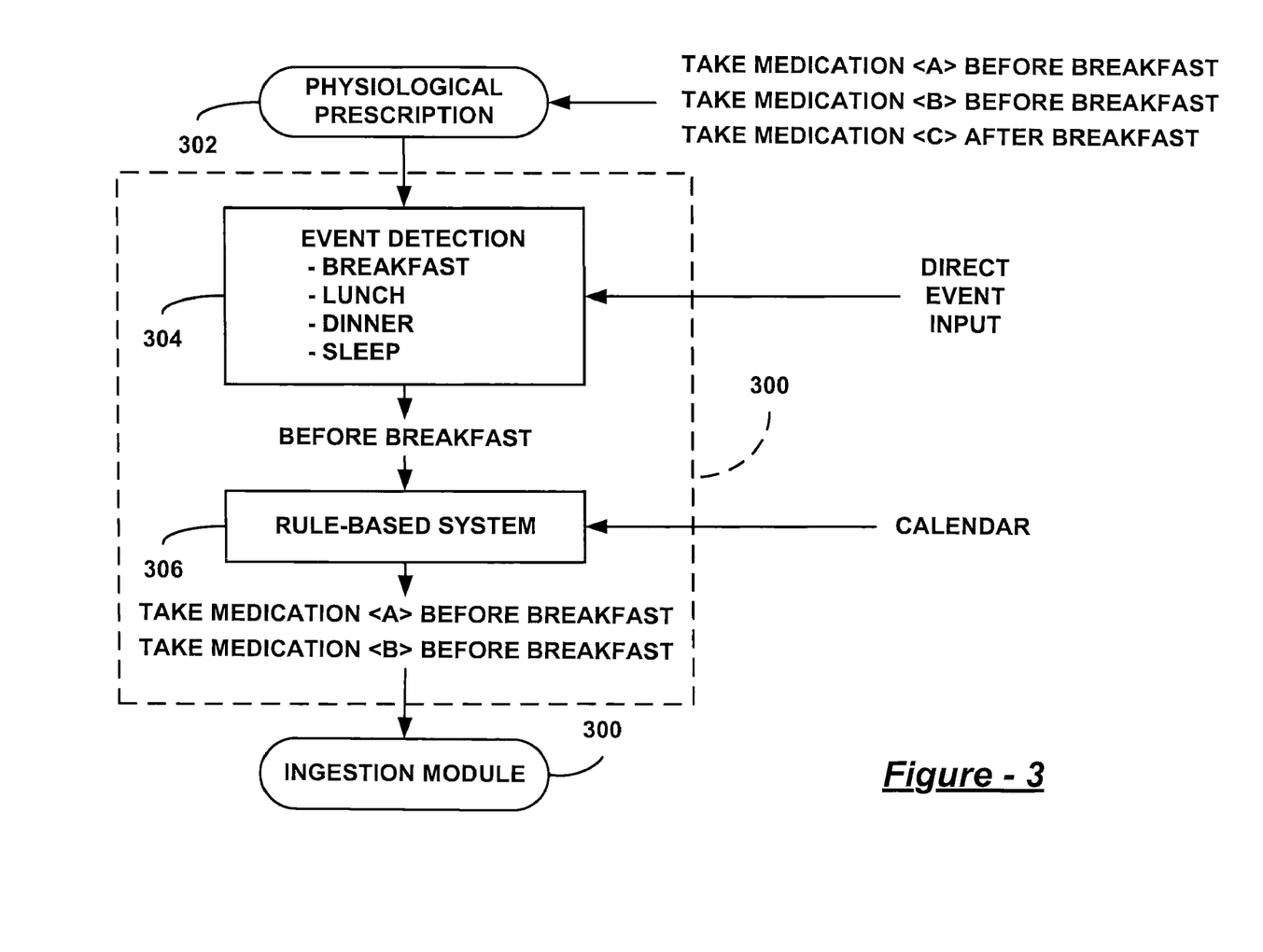
FIG. 3 is a block diagram illustrating a physiological module of a medication dispenser.

Turning now to FIG. 3, a physiological module 300 takes as input an event-based e-prescription, and forwards it to an event detection module 304, which determines the events to come. These events are sent to a rule-based mechanism 306 selecting the rules to be used to handle this event. The rule based mechanism 306 filters the rules provided in the e-prescriptions according to the triggering event, and provides the list of event-based medication to be dispensed. For example, in FIG. 3, medication <A> and<B> should be dispensed at event "before breakfast." The list of medication to be dispensed is forwarded to the ingestion module, which determines the final doses to be dispensed and the time on which to administer them.

When starting use of the medication dispenser, the user can, for example, indicate all events (breakfast, lunch, dinner, sleep) in real-time through a simple interface. Alternatively or additionally, the user can enter these elements into a weekly calendar. The event detection module 304 can start with these indications and determine events based on them, knowing that the user always over-rules the calendar. The user can also annotate some events as exceptional, so that they do not introduce a bias into the learning process.

The event detection module 304 can maintain its own dynamically adjusted calendar. It can, for example, note new input times for each event, and make a determination of the time ranges in which these events occur. In some embodiments, the application of simple statistics can provide the most probable time for the next occurrence of an event, based on its history.

Consider, for example, that Table 1 records every occurrence of the breakfast, lunch and diner events of a patient. This table can calculate the range of these events (e.g., Monday breakfast between 6:30 and 7:00), and average time is 6:45.

TABLE 1

| Events | Mon. | Tues. | Wed. | Thurs. | Fri. | Sat. | Sun. |
|---|---|---|---|---|---|---|---|
| Breakfast | 6:30; 6:45; 7:00 | | | | | | |
| Lunch | | | | | | | |
| Dinner | | | | | | | |

As such, after a short learning period the Event Detection module 300 can acquire statistical information on simple user-habits like meals, sleep, etc. This information is sufficient to predict the time of the <before> <during> <after> events and to schedule medication dispensing accordingly.

Figure 4:
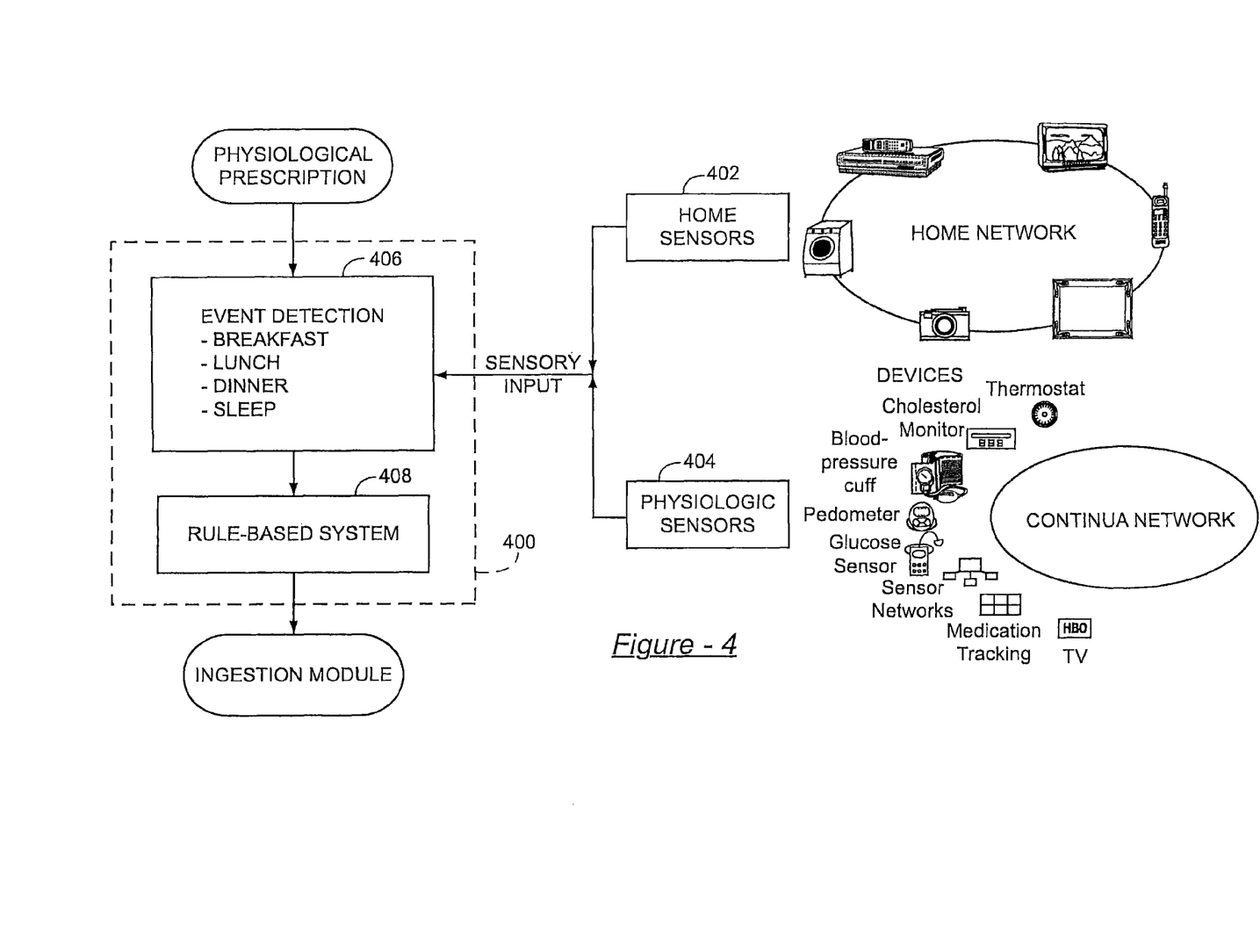
FIG. 4 is a block diagram illustrating home sensors and physiological sensors providing input to a physiological module of a medication dispenser.

Turning now to FIG. 4, after this initialization, the medication dispenser 400 can additionally be connected to sensory networks, like home sensors 402 of a home network and medical sensors 404 of a medical network, for which the Continua Alliance standard provides an exemplary instance. In the case of a home network, it is envisioned that motion detectors, for example, of a security system can be used to track movement of the user in the home and observe behavior that indicates sleep and meals. Alternatively or additionally, operation of appliances (e.g., microwaves, televisions, and/or dishwashers) connected to the home network can be observed. Alternatively or additionally, use of a telephone connected to the home network to call a restaurant can be observed. Alternatively or additionally, GPS of a device (e.g., medication dispenser, cell phone, automobile, navigation system, etc.) accompanying the user can be observed and used in conjunction with additional information. For example, map information can be used to determine that the user is at a restaurant. As another example, positive and negative feedback can be used to determine if the user is currently at a location, and/or headed toward a location, or headed away from a location at which user ingestion normally does or does not occur.

It is additionally or alternatively envisioned that peripheral devices can be provided for use as sensors supplying input to the medication dispenser 400. For example, contact, motion, and/or photo sensors can be provided that can detect opening of cabinets, opening of doors, and/or opening of a refrigerator. In this way, the system can learn, for example, that opening of one or more of these access points can indicate a meal. Alternatively or additionally, the system can learn that opening of a door, followed by a flurry of cabinet and refrigerator openings, such as when the user returns from the grocery store, does not indicate a meal.

The aforementioned additional sensory parameters can be linked to

| | Mon. | Tues. | Wed. | Thurs. | Fri. | Sat. | Sun. |
|---|---|---|---|---|---|---|---|
| Breakfast | 6:30; 6:45; 7:00 | | | | | | |
| Lunch | | | | | | | |
| Dinner | | | | | | | |

Table 1 to enrich it as well as to structure the learning part linked to this table. For example, starting from the simple

| | Mon. | Tues. | Wed. | Thurs. | Fri. | Sat. | Sun. |
|---|---|---|---|---|---|---|---|
| Breakfast | 6:30; 6:45; 7:00 | | | | | | |
| Lunch | | | | | | | |
| Dinner | | | | | | | |

Table 1, sensory elements can be added around the events (like breakfast) to provide a richer description of the event. An example of such sensory elements is shown in Table 2, where microwave use and TV use are added to the breakfast event.

TABLE 2

Enriched Event Table

| | Monday | Tuesday | Wed. | Thurs. | Friday | Sat. | Sunday |
|---|---|---|---|---|---|---|---|
| Breakfast | 6:30; 6:45; 7:00 | 6:30; 6:50; 7:10 | 6:00; 6:02; 6:00 | 6:30; 6:45; 7:00 | 6:30; 6:45; 7:00 | 8:00; 8:10; 7:50 | 8:00; 8:10; 7:50 |
| Sensory input | Microwave | Microwave | Microwave TV News | Microwave | Microwave | | |
| Lunch | 12:30; 13:45; 13:00 | | | | | | |
| Dinner | 20:00 | | 18:00; 18:12 | | | | |

Simple correlation mechanisms between the events (e.g. breakfast) and the sensory input provide an elementary event detection mechanism. In the example, a use of the microwave around 6:30 AM on Monday, Tuesday, Thursday and Friday can be correlated with the breakfast. For Wednesdays, the breakfast is correlated with the use of the microwave and the TV news at around 6:00.

Processes for learning such regularities can involve a correlation. They can alternatively or additionally use statistical methods, Bayesian methods, and/or grammars and tree search methods to discriminate the classes of examples and counter examples. Engineers knowing the state of the art in data mining statistics can implement these methods based on the templates provided above.

As mentioned above, certain sensory events can be directly measured by sensors (e.g. blood pressure, blood glucose . . . ). Those measures can be directly compared to alert thresholds. If a threshold is reached, the event detection module 406 can immediately sends events to the rule-based system 408.

In some embodiments, the rule-based system 408 can be a classic first order rule-based system incorporating the notion of time. One possible implementation is to use the fuzzy controllers developed in fuzzy logics, and commonly applied to rice-cookers and washing machines.

Figure 5:
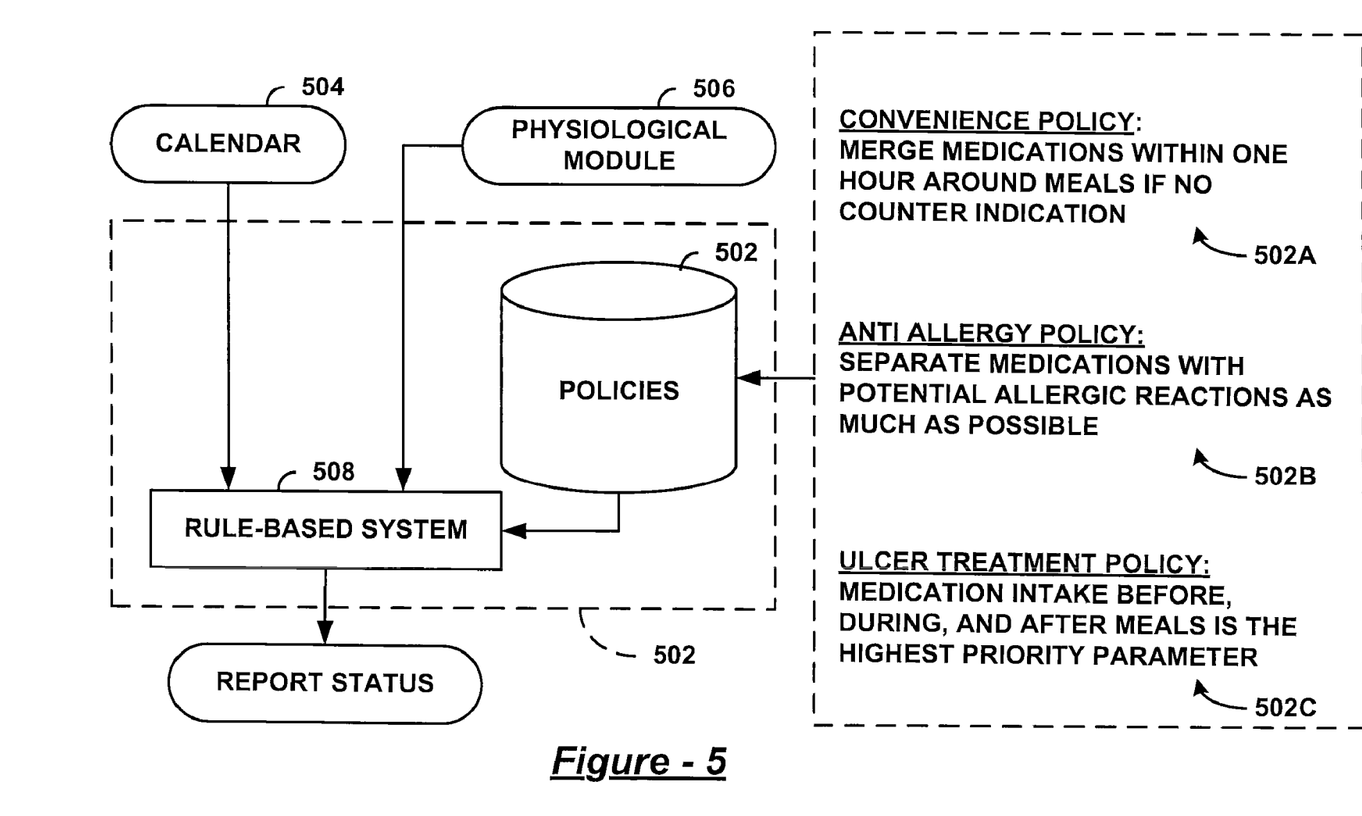
FIG. 5 is a block diagram illustrating an ingestion module of a medication dispenser.

Turning now to FIG. 5, the ingestion module 500 can dispense time-based and event-based medication independently using a calendar for the time-based medication and administering event-based medication at the events when they are detected. However, in some embodiments, the medications can be merged into doses to ease the life of patients and optimize these doses according to some policies 502. The ingestion module 500 can fulfill this function.

The ingestion module 500 can take as input the medications to be dispensed on time-bases provided by the calendar 504 as well as the event-driven mechanisms provided by the physiological module 506. Both can be entered into a rule-base system 508 evaluating policies 502 implemented as rules. Examples of such policies can be: convenience 502A (minimizing the number of medication intake), anti-allergy 502B (making sure to minimize known allergic reactions and incompatibility between medication), and/or Ulcer-treatment policy 502C (where medication intake is fine tuned for minimum impact on the stomach). Other example policies can minimize affect on kidneys, liver, etc. These policies can tailor medication intake to the patient condition, knowing that some patients might well respond to one policy and less to another. In some embodiments, medical doctors, nurses, and/or pharmacists can define these policies for their patients.

Figure 6:
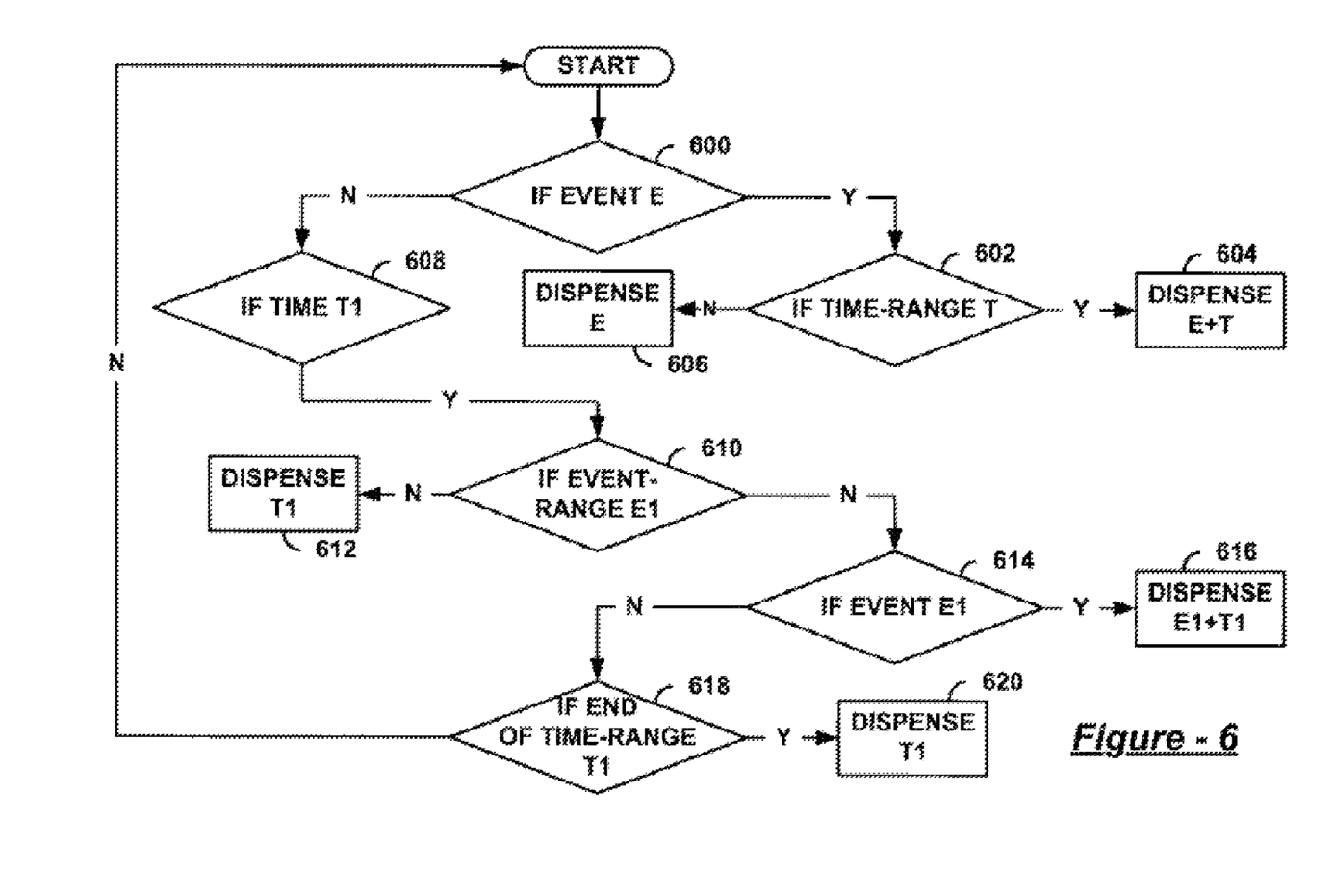
FIG. 6 is a flow diagram illustrating a method of operation for use with an ingestion module of a medication dispenser.

Turning now to FIG. 6, a convenience policy can be implemented, for example, by introduction of a time-range period for administering both time-based and event-based medication. Regarding time-based medication, for example, the time-range can be the time period in which it is suitable to ingest the medication. Also, regarding event-based medication, the event-range can be the estimated time period for this event. A computer implemented process can exploit opportunities to merge medications. For example, when an event appears at decision step 600, the process can seek for time-related medication having a time range that overlaps with the estimated time range at decision step 602, and dispense both medications together at step 604. Otherwise, the event-based medication can be dispensed alone at step 606. Additionally, if it is time to dispense a time-based medication at decision step 608, the time-based medication can be dispensed alone at step 612 if it is determined at decision step 610 that no time range of any event-based medication overlaps with the time range of the time-based medication. However, if it is determined that there is an overlapping time range at decision step 610, the process can postpone dispensing the time-based medication until it is determined at decision step 614 that the event has occurred, and thus dispense the time-based medication and the event-based medication together at step 616. While the event is not determined to have occurred at decision step 614, the process can decide at decision step 618 to postpone as much as possible the ingestion of the time-based medication, hoping that it can merge it with the event-based medication. However, if no event appears at step 614, the time-based medication can be dispensed at step 620 when the end of its time-range is determined to have been reached at decision step 618. This process can reduce the number of medication intake occurrences, hence improving the comfort and convenience of patients.

Figure 7:
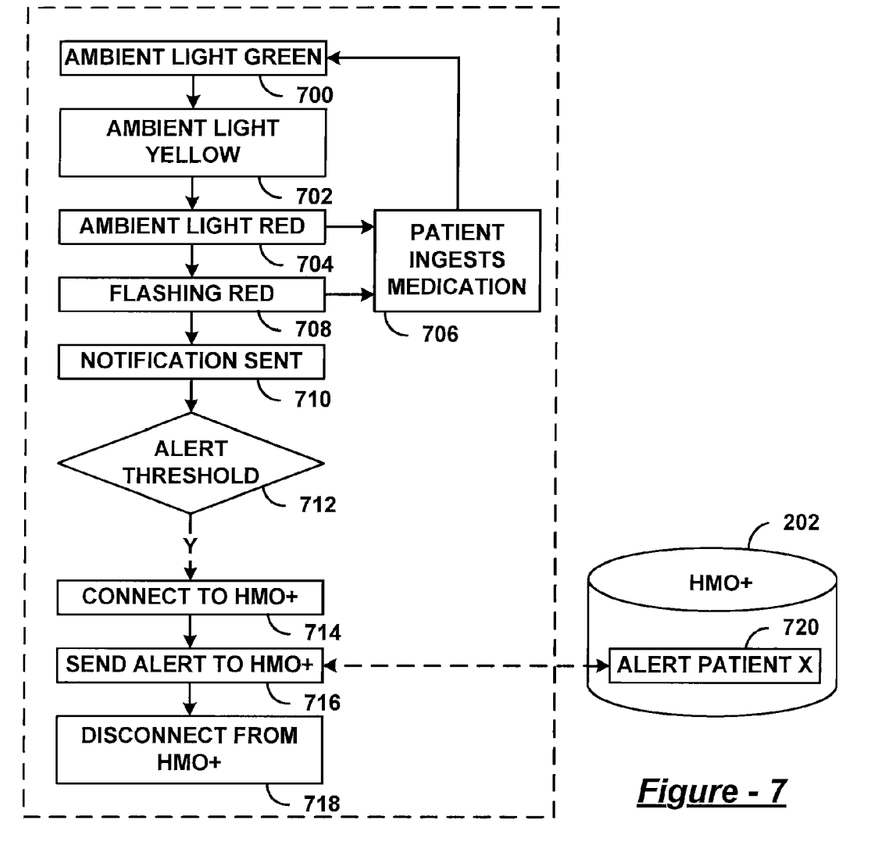
FIG. 7 is a flow diagram illustrating a method of operation for an ambient medication dispenser in communication with an HMO+.

Turning now to FIGS. 2 and 7 and referring generally thereto, some embodiments of the dispenser can be made ambient, providing light colors for different phases of medication intake. For example, a green light display at step 700 can change to a yellow light display at step 702 when a time range for ingestion of a medication has been entered. This light display can then switch to a red light display at step 704 when an end of a time range for taking the medication has been reached. At this point, if the patient takes the medication at step 706, the light display can switch back to display of green light at step 700. However, if the patient does not take the medication in a predetermined amount of time, the display can switch to a flashing red light at step 708. Then, if the patient takes the medication at step 708 within another predetermined amount of time, the light display can return to green at step 700. However, if the patient does not take the medication within the other amount of time, then notifications can be periodically or continuously sent to module 210 at step 710. If a time-based alert threshold is reached at step 712, then module 710 can connect to the HMO+ 202 at step 714, send an alert to the HMO+ 202 at step 716, and disconnect from the HMO+ at step 718. The HMO+ can record the alert regarding the patient in a computer readable medium at step 720.

From the foregoing description, it should be readily understood that one or more embodiments of a device can be realized that is capable of sorting, preparing, and checking the medication doses for a patient according the patient's physiological cycle. Some embodiments of the device can detect, for example, the meal and sleep patterns and automatically adapt the medication ingestion to the patient's routine while following the e-prescription. In addition the medication intake can be tailored in some embodiments to the patient through policies capable of dealing with allergies, personal preferences, and specific conditions.

It should also be readily understood that numerous benefits to users can be accomplished in some embodiments. For example, optimal follow-up of ingestion prescription can be realized. This follow-up can translate into an increase of medication effect while observing a decrease of side effects. These results can additionally be obtained in concert with adaptation to particular conditions like allergies, stomach, liver, and kidney issues. Users can further be provided with more freedom in their schedules.

It should further be readily understood that numerous benefits to HMO+ can be accomplished in some embodiments. For example, a reduction of costs can be achieved by increase of proper medication intake of patients. Also, feedback on effective medication intake can be realized, allowing a better monitoring of patients.

What is claimed is:

1. A medication dispensing system for use with a medication dispenser, the system comprising:
   a physiological module implemented as computer executable instructions executed by a computer processor of a computing device, the physiological module receiving an event-based medication prescription for a patient that specifies when to ingest a first medication in relation to a physiological event experienced by the patient and receiving sensory input from one or more sensors remote from the computing device and proximate to the patient, the physiological module detecting a pattern of occurrences of the physiological event from the sensory input, identifying an expected time for an occurrence of the physiological event and scheduling ingestion of the first medication proximate the expected time for the occurrence of the physiological event and in accordance with the event-based medication prescription;
   wherein said physiological module includes an event detection module that maintains a calendar of events experienced by the patient, including the physiological event, and makes a determination of a time range in which these events occur; and
   an ingestion module that receives another time-based medication prescription for the patient that specifies a timing for ingesting a second medication, the ingestion module schedules ingestion of the second medication in relation to the ingestion of the first medication in accordance with an ingestion policy,
   said ingestion module employs a predetermined temporal window for dispensing the second medication to determine whether to delay or accelerate dispensing the second medication and delays dispensing of the second medication when overlap occurs with the expect time for the occurrence of the physiological event.

2. The system of claim 1, wherein said ingestion module delays dispensing of the second medication until either: (a) the first medication is dispensed or (b) an end of the predetermined temporal window is reached, whichever comes first.

3. The system of claim 1, wherein said system downloads an e-prescription from a health monitoring organization, and the e-prescription specifies both the information regarding intake of the second medication, and the information regarding the event-based medication prescription.

4. The system of claim 3, wherein the information regarding intake of the second medication includes instructions for dispensing medication according to a fixed time distribution schedule, and the event-based medication prescription includes instructions for dispensing medication in response to events including at least one of: blood pressure level; heart attack; going to sleep; waking; and taking a meal.

5. The system of claim 1, wherein said ingestion module recognizes that the second medication and the first medication have a possibility of producing a side effect when consumed concurrently, and decides to delay or accelerate dispensing of the second medication in order to increase a time difference between ingestion of the second medication and ingestion of the first medication.

6. The system of claim 5, wherein the side effect is an allergic reaction.

7. The system of claim 1, wherein said system connects to a health monitoring organization and uploads notifications of medication intake in order to update status of the patient.

8. A medication dispensing method for use with a medication dispenser, the method comprising:
  receiving an event-based medication prescription for a patient that specifies when to ingest a first medication in relation to a physiological event experienced by the patient;
  receiving sensory input from one or more sensors proximate to the patient;
  detecting a pattern of occurrences of the physiological event from the sensory input by a physiological module executed by a computer processor;
  identifying an expected time for an occurrence of the physiological event from the pattern of occurrences;
  scheduling ingestion of the first medication to correlate with the expected time in accordance with the event-based medication prescriptions and an ingestion policy by an ingestion module executed by the computer processor;
  maintaining a calendar of events experienced by the patient, including the physiological event, and making a determination of a time range in which these events occur;
  receiving a time-based-medication prescription for the patient that specifies a timing for ingesting a second medication and employing a predetermined temporal window for dispensing the second medication to determine whether to delay or accelerate dispensing the second medication; and
  delaying dispensing of the second medication when overlap occurs of the predetermined temporal window with the expected time for an occurrence of the physiological event.

9. The method of claim 8, further comprising delaying dispensing of the second medication until either: (a) the first medication is dispensed or (b) an end of the predetermined temporal window is reached, whichever comes first.

10. The method of claim 8, further comprising downloading an e-prescription from a health monitoring organization, wherein the e-prescription specifies both the information regarding intake of the second medication, and the information regarding the event-based medication prescription.

11. The method of claim 10, wherein the information regarding intake of the second medication includes instructions for dispensing medication according to a fixed time distribution schedule, and the event-based medication prescription includes instructions for dispensing medication in response to events including at least one of: blood pressure level; heart attack; going to sleep; waking; and taking a meal.

12. The method of claim 8, further comprising:
  recognizing that the second medication and the first medication have a possibility of producing a side effect when consumed concurrently; and
  deciding to delay or accelerate dispensing of the second medication in order to increase a time difference between ingestion of the second medication and ingestion of the first medication.

13. The medication dispensing method of claim 8 wherein detecting a pattern of occurrences of the physiological event further comprises learning a pattern of meal times for the patient and scheduling ingestion of the medication to correlate with the pattern of meal times.

14. The medication dispensing system of claim 1 wherein the ingestion policy is further defined as a convenience policy that minimizes a number of medications taken.

15. The medication dispensing system of claim 1 wherein the ingestion policy is further defined as an anti-allergy policy that separates in time ingestion of medications having potential allergic reactions.

* * * * *

UNITED STATES PATENT AND TRADEMARK OFFICE
CERTIFICATE OF CORRECTION

| | | |
|---|---|---|
| PATENT NO. | : 8,068,015 B2 | Page 1 of 1 |
| APPLICATION NO. | : 11/843306 | |
| DATED | : November 29, 2011 | |
| INVENTOR(S) | : Bernard Burg | |

It is certified that error appears in the above-identified patent and that said Letters Patent is hereby corrected as shown below:

In column 8, line 66, claim 1, delete the word "expect" and insert --expected--

Signed and Sealed this
Twenty-eighth Day of February, 2012

David J. Kappos
*Director of the United States Patent and Trademark Office*